United States Patent [19]

Platt

[11] Patent Number: 5,759,992

[45] Date of Patent: Jun. 2, 1998

[54] IMMUNOTHERAPEUTIC AGENT DERIVED FROM BACTERIA AND METHOD FOR ITS MANUFACTURE

[75] Inventor: David Platt, 33973 Old Timber Rd., Farmington Hills, Mich. 48331

[73] Assignee: David Platt, Farmington Hills, Mich.

[21] Appl. No.: 612,307

[22] Filed: Mar. 7, 1996

Related U.S. Application Data

[63] Continuation of Ser. No. 299,145, Aug. 31, 1994, Pat. No. 5,527,770.

[51] Int. Cl.$^6$ .............. A61K 38/00; C12N 1/00; A23J 1/00

[52] U.S. Cl. ............... 514/2; 514/21; 514/885; 435/243; 435/252.33; 435/253.1; 435/849; 435/863; 530/412; 530/413; 530/414; 530/418; 530/427; 424/248.1; 424/257.1

[58] Field of Search ............... 514/2, 21, 885; 435/243, 252.33, 253.1, 849, 863; 530/322, 412, 413, 414, 418, 427; 424/248.1, 257.1

[56] References Cited

U.S. PATENT DOCUMENTS

| | | | |
|---|---|---|---|
| 4,726,947 | 2/1988 | Shimada et al. | 424/92 |
| 5,116,614 | 5/1992 | Ehrenfeld | 424/92 |
| 5,182,109 | 1/1993 | Tamura et al. | 424/92 |
| 5,527,770 | 6/1996 | Platt | 514/2 |

OTHER PUBLICATIONS

Bennett et al.; "A comparison of commerically available adjuvants for use in research"; J. Immunological Methods 153 (1992) 31–40.

Yang et al.; "Prevention of adjuvant arthritis in rats by a nonapeptide from the 65–kD mycobacterial heat–shock protein"; Clin. exp. Immunol. 81 (1990) 189–194.

Fikrig et al.; "Protection of Mice from Lyme Borreliosis by Oral Vaccination with *Escherichia coli* Expressing OspA"; JID 1991; 164; 1227–32.

Paque et al.; "Polyclonal Anti–Idiotypic Antibodies Exhibit Antigenic Mimicry of Limited Type 1 Fimbrial Proteins of *Escherichia coli*"; Infection and Immunity; V58, No. 3 (1990) 680–686.

Hubbard et al.; "Immunization of mice with mycobacterial culture filtrate proteins". Clin. exp. Immunol. (1992) 87, 94–98.

Chowdhury et al.; "The *Mycobacterium bovis* BCG 64–kDa surface protein is antigenically shared with different mouse tumor cells and has anti–tumor activity in immunized mice". Immunology Letters 36 (1993) 235–238.

Kingston et al.; "Immunological Activity of a 14–Kilodalton Recombinant Protein of *Mycobacterium tuberculosis* H37Rv"; Infection and Immunity Dec. 1987; 3149–3154.

Kaufmann et al.; "Enumeration of T cells reactive with *Mycobacterium tuburculosis* organisms and specific for the recombinant mycobacterial 64–kDa protein"; Eur. J. Immunol. 1987; 17:351–357.

Constant et al.; "Stimulation of Human γδ T Cells by Nonpeptidic Mycobacterial Ligands"; Science 264; 8 Apr. 1994; 267–270.

Primary Examiner—Cecilia J. Tsang
Assistant Examiner—Abdel A. Mohamed
Attorney, Agent, or Firm—Gifford, Krass, Groh, Sprinkle, Patmore, Anderson & Citkowski, P.C.

[57] ABSTRACT

An immunotherapeutic agent is prepared from cells of *E. coli* or members of the genus Mycobacterium. The material is effective as an anti-tumor agent, an immunostimulant, and an adjuvant. Also disclosed is a method of evoking an immunostimulatory response through the activation of the RAS gene.

12 Claims, 1 Drawing Sheet

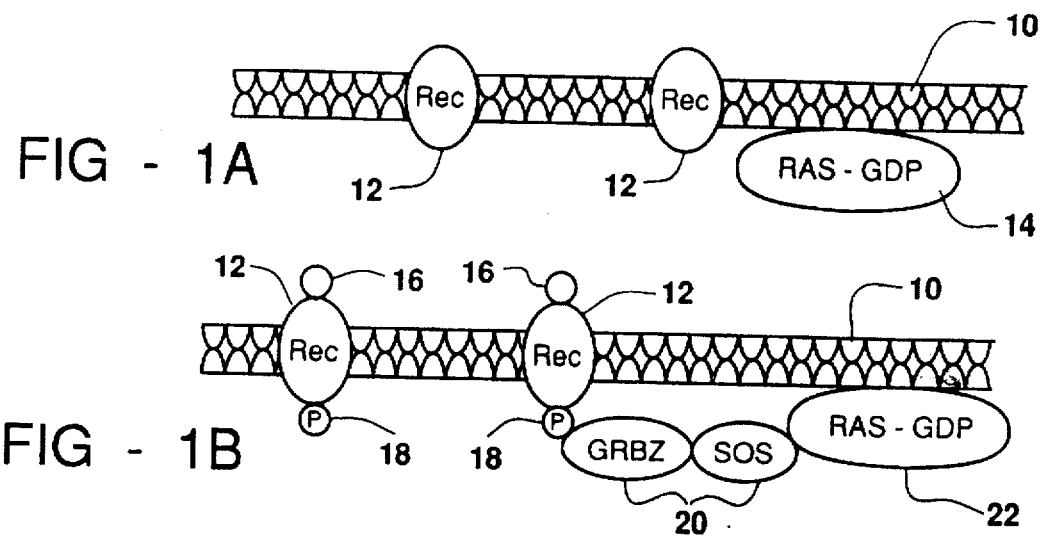
FIG - 1A
FIG - 1B
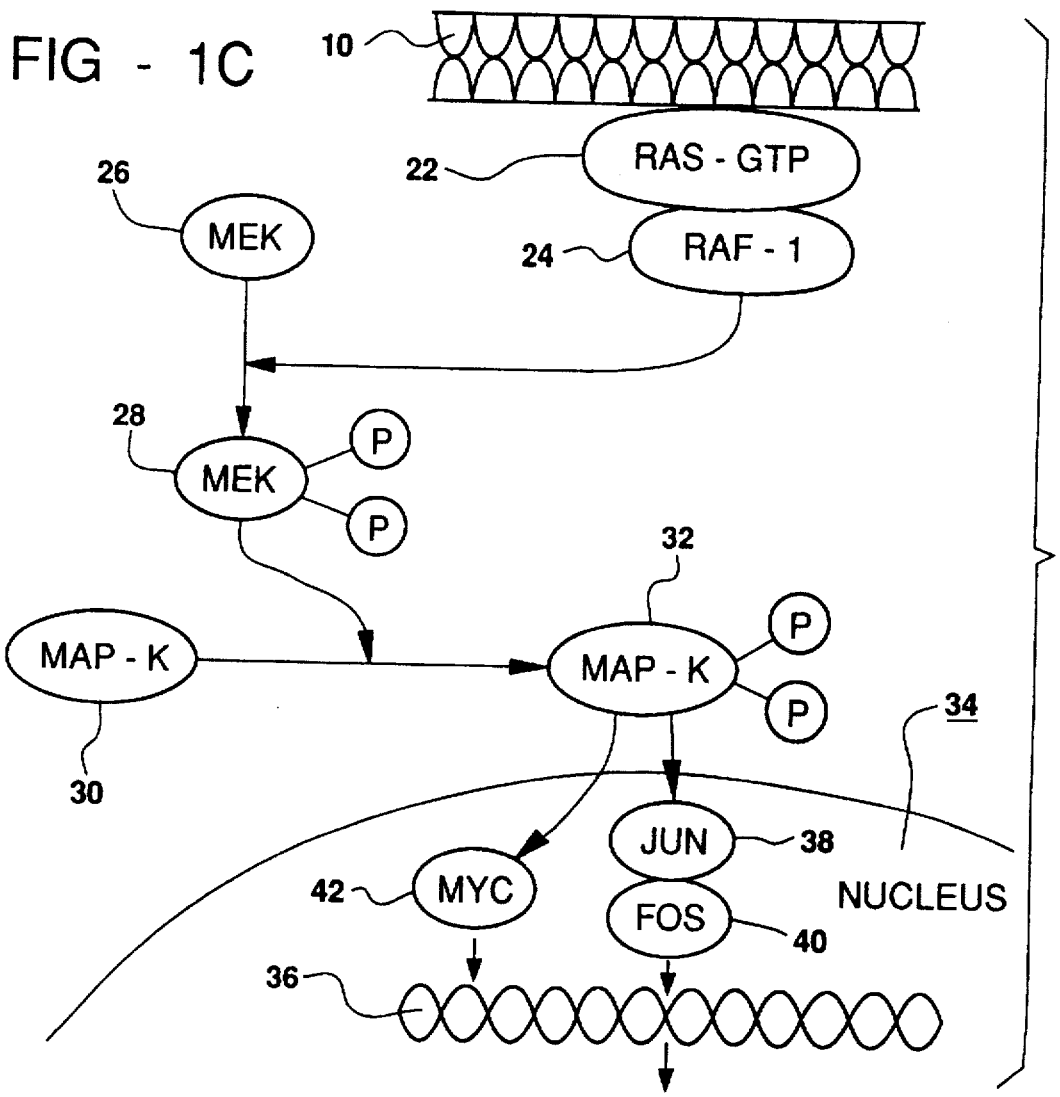
FIG - 1C

IMMUNOTHERAPEUTIC AGENT DERIVED FROM BACTERIA AND METHOD FOR ITS MANUFACTURE This application is a continuation of application Ser. No. 08/299,145, filed Aug. 31, 1994, now U.S. Pat. No. 5,527,770.

FIELD OF THE INVENTION

This invention relates generally to a bacterial cell preparation which manifests anti-tumor, adjuvant and immunostimulatory properties, and to methods for the preparation of the material.

BACKGROUND OF THE INVENTION

The role of the immune system is critical in the control of diseases such as cancer, as well as diseases caused by external agents such as virus or bacteria. Presently, there is great interest in the use of therapeutic materials which can enhance the response of the immune system, particularly with regard to the treatment of cancer and AIDS. It has been known for some time that various bacteria manifest a strong anti-tumor and immunostimulatory effect. Also, it has been found that these bacteria can also act as an adjuvant material. An adjuvant is a material which, when introduced into an animal, along with an antigen, evokes and enhance production of antibodies to that antigen.

Various bacterial preparations have been investigated for use as immunostimulatory agents. Freund's Complete Adjuvant (CFA) was developed in the early 1950's. It comprises a crude preparation of a bacteria of the genus Mycobacterium, particularly M. tuberculosis. CFA has been found to be a relatively potent adjuvant and has become a research standard; however, its use as a therapeutic agent, and in some instances its use as a research material, has been limited by the fact that it is quite toxic. In an attempt to overcome the toxicity of CFA, various other adjuvant materials have been developed; for example, as disclosed by Bennett et al. in "Journal of Immunological Methods" 153 (1992) 31–40, a synthetic material comprising a water in oil emulsion of squalene together with a particular block copolymer has been found to have adjuvant activity. This material is still somewhat toxic and it is employed in a non-aqueous base and hence of limited utility.

Various bacterial preparations have been developed in an attempt to improve upon CFA. As disclosed in U.S. Pat. No. 4,726,947, a relatively high molecular weight extract of various species of Mycobacterium has been found to have adjuvant and anti-tumor effects. As disclosed in U.S. Pat. No. 5,116,614, cell wall preparations of the bacterial genus Nocardia have adjuvant and anti-tumor effects when coupled with particular synthetic molecules.

All the prior art adjuvant and anti-tumor materials have been found to be less than adequate for clinical applications. The immunostimulatory effect of prior art materials is generally far less than that of CFA. Furthermore, many of these materials are toxic and difficult to prepare. Furthermore, most are not aqueous based and, hence, their use is further complicated. It will be appreciated that there is a need for an immunotherapeutic agent which is of high activity and low toxicity. The agent should also be easy to prepare and administer. The present invention provides an immunotherapeutic agent derived from bacterial cells. The agent is highly active and of low toxicity. Its preparation is relatively simple and it is a stable, aqueous based material. These and other advantages of the present invention will be readily apparent from the discussion which follows:

BRIEF DESCRIPTION OF THE INVENTION

There is disclosed herein a method for preparing an immunotherapeutic agent. The method comprises the steps of culturing cells of a bacterium selected from the group consisting of E. coli, and members of the genus Mycobacterium. The cells are collected and their membranes disrupted, as for example by ultrasonic energy. The disrupted cells are separated into sediment and supernatant liquid. The supernatant liquid is flocculated so as to produce a solid material. The solid material is separated into a first fraction having a molecular weight of more than 85,000 daltons and a second fraction having a molecular weight of less than 85,000 daltons. The second fraction contains the immunotherapeutic agent. The agent is believed to include a material which has a molecular weight of 919.2 daltons and comprises a glycopeptide, and may also include a second material which has a molecular weight of approximately 65 kilodaltons and comprises a glycosylated protein. It is believed that the therapeutic effects of the present invention are due to these two materials either taken singly or in combination.

There is also disclosed herein a method for simulating the immune system of a cell. The method involves the activation of the RAS/RAF-1/MAP-Kinase pathway of the cell.

BRIEF DESCRIPTION OF THE DRAWING

FIGS. 1A–1C comprise a schematic depiction of one proposed mode by which the LMG of the present invention operates to activate the immune system.

DETAILED DESCRIPTION OF THE INVENTION

The present invention relates to an immunotherapeutic agent having anti-tumor as well as adjuvant activity. The agent is derived from bacteria. The most preferred bacteria comprise members of the genus Mycobacterium with one particularly preferred material being M. tuberculosis. Other members of the genus comprise M. Avium, M. Bovis and M. Smegmatis. It has also been found that the agent can be prepared from E. coli. It is believed that the active material comprises a glycopeptide and/or a glycosylated protein. In the context of the present disclosure, the material of the present invention will be referred to as "LMG (low molecular weight glycopeptide)." At present, the precise structure of the LMG has not been elucidated; however, parameters for its preparation are well defined. The active material may include a first species of low molecular weight, i.e., approximately 919.2 daltons as determined by mass spectroscopy. The basic structure of the first species as determined by 2-d nuclear magnetic resonance is thought to be:

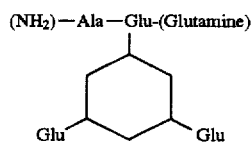

although it is to be understood that the structure of the material prepared in accord with the invention may actually be found to be different. The LMG may also include a second active species which has a molecular weight of about 65 kilodaltons and comprises a glycosylated protein. Either of the species, or the two in combination, are responsible for the action of the LMG.

The LMG may be prepared from a number of Mycobacterium species with M. tuberculosis being one particularly preferred bacteria. It has also surprisingly been found that the LMG can be isolated from *E coli.*

The LMG was prepared from *M. tuberculosis* strain H37Ra as follows: the bacteria was grown in culture medium in accord with standard procedures well known in the art. No particular restrictions are imposed on the method of growing the microorganism and various media such as Sauton's medium or glycerin-boullion medium may be employed. The bacteria are filtered from the culture and dried to provide a powder. The powder is suspended in water and disrupted, for example, as by the input of ultrasonic energy. Care is taken that the sample be maintained at a temperature of 4° C. or less during the sonication process, so as to maximize yield of LMG.

The emulsion resultant from the disruption is stirred for 48 hours, while being maintained at a temperature of 4° C. or less, after which it is centrifuged at 14000 rpm for 10 minutes, while being maintained at no more than 4° C. The supernatant is collected and freeze dried, again at a temperature of no more than 4° C., to produce a dry material.

The freeze dried material is dissolved in water at an approximate concentration of 20 milligrams per milliliter. The solution is maintained at 4° C. and cold acetone is added dropwise with stirring. The total amount of acetone added is twice the volume of the water. When the addition of acetone is completed, the vessel is tightly covered to protect it from the atmosphere and the solution is stirred for 24 hours. Care is taken during the addition of acetone and the subsequent stirring to maintain the temperature at no more than 4° C. The solution resultant from these steps appears homogeneous.

The solution is centrifuged at 14,000 rpm for 10 minutes, at a temperature no more than 4° C. The supernatant solution is discarded and the precipitated pellet is dissolved in water and freeze dried. The LMG is contained in this material.

The LMG is isolated by dissolving the freeze dried pellet material in distilled water, at an approximate concentration of 1 milligram/milliliter. The dissolved material is then ultra filtered through a filter having a molecular weight cut-off point of approximately 85,000 daltons. The material which passes through the filter comprises the LMG of the present invention.

In a variation of the above described process, the ultra filtration step may be replaced by high pressure liquid chromatography separation for the isolation of the LMG.

The LMG has been found to have very good anti-tumor activity. BALB/C mice were injected with B 1/6-F1 melanoma cells. After three injections of the LMG the primary tumor disappeared and no metastasis was detected in the lung. In another experiment, NO/NO mice were injected with C-8161 human melanoma, and after the tumor grew to approximately 4 millimeters, the mice were injected with LMG four times, at an interval of three days, after which no tumors were detected in the lungs and the primary tumor at the injection site had disappeared. In another experiment, PC-3-1A human prostrate carcinoma cells were injected into nude mice. These cells typically will form multiple microscopic tumor colonies in such mice after intravenous injection. In this experimental series, the mice were injected with 20 milligrams of LMG in a PBS buffer 24 hours after the tumor cell line. The injection of the LMG was repeated five days later and no tumors were detected in the lungs or at the primary injection site.

The LMG has been found to be a potent adjuvant. It can be injected into animals by itself, typically in the form of a solution with PBS buffer, or together with an antigen. It has been found that the antibody titer resultant from the use of LMG is twice that of CFA, and no toxic reactions were detected. The typical amounts employed are 20 micrograms per 0.2 Ml.

The immunostimulatory effect of the material of the present invention is of significant utility in the treatment of AIDS. It has been found in animal tests that LMG causes extensive proliferation of $\gamma$S and $\alpha\beta$ T cells, an increase in the number of CD4 and T1 helper cells in the lymph nodes, an increase in interferon $\gamma$ and a 30 fold increase in IL-2.

The immune system includes CD4 and CD8 cells in a generally fixed ratio. It is believed that when new cells are generated in the immune system, no distinction is made between the CD4 and CD8 cells. The AIDS virus only attacks the CD4 cells, thereby decreasing their numbers. In response to the decreasing level of CD4 cells, the body generates new CD4 cells, together with CD8 cells. The rise in CD8 cells serves to limit the generation of further cells, including CD4 cells. Therefore, the CD4 level never rises fully and the strength of the immune system ultimately declines as a result of the homeostatic balance of the immune cells.

It has been found that the material of the present invention is an immunostimulant which can actually alter the ratio of CD4 to CD8 cells. In mice the normal ratio of CD8 to CD4 is in the range of 1:1.5 to 1:2. Eleven mice were injected with LMG. In 11 out of 11 mice it was found that the ratio of CD8:CD4 was raised to 1:4.

It has been determined, based upon experimental evidence, that the LMG of the present invention operates in a growth hormone-like manner to stimulate the immune system. This novel mode of action presents a heretofore unavailable biochemical pathway for the moderation of immune system response.

Referring now to FIGS. 1A–C, there is shown, in schematic form, the operation of the present invention. FIG. 1A depicts a portion of a cell membrane of a B cell. As is well known, the membrane 10 comprises a bi-layer, and it includes a number of receptors 12 therein. The receptors are of different types, and are specific for various molecules. Associated with the cell, interiorally of the membrane 10, is a gene known as RAS. The RAS gene has previously been identified as being associated with cell growth and differentiation, and it can function as an oncogene. The RAS gene is in the GDP complex form, 14, all of said terms being well known in the art.

In the first step, as shown in FIG. 1B, the LMG of the present invention 16, binds two particular receptors 12 on the cell membrane 10. The LMG activates the receptors so as to provide a phosphate 18, typically in the form of tyrosine phosphate. The activated receptors bind to the GRB2-SOS complex 20 which in turn activates the RAS gene, which to produce the RAS-GTP complex 22.

As is shown in FIG. 1C, the RAS-GTP complex 22 activates RAS-1 kinase, 24, possibly with help from a small number of other proteins. RAS-1 kinase, 24, in turn, activates the MAP kinase cascade which activates the appropriate gene 36 which directs the release of transcription factors and other cellular proteins that bring about the cell response. Specifically, RAS-1 kinase 24 activates the phosphorylation of MEK 26 to MEK-P 28; and MEK-P 28 activates the phosphorylation of MAP-K 32 to MAP-K-P 32. The phosphorylated MAP-K 32 acts within the cell nucleus 34 to activate a specific gene 36. Activation occurs through cellular proteins and transcription factors JUN 38, FOS 40 and MYC 42, and possibly others. Activation of the gene 36 brings about the release of novel proteins which lead to the proliferation of various lymphocytes.

The foregoing mechanism has been supported experimentally. It has been found that the LMG of the present invention is operative even when the major histocompatibility complex MHC in B cells is blocked by actinomycin. It would normally be expected that blocking of MHC in the B cells would inhibit T cell proliferation. Therefore, the activation of the B cells by the LMG must not proceed along the MHC pathway. It has further been found that when human white blood cells are incubated for ten minutes with the LMG of the present invention, the level of tyrosine phosphate increases, which is indicative of formation of the REC-P complex. Also, it has been found that in the same cells, the level of MAP-K-P increases.

Thus, it will be seen that the present invention provides a novel pathway whereby the RAS gene may be activated so as to activate leukocyte proliferation via a growth hormone-like pathway. While activation is accomplished by the LMG of the present invention, it will be appreciated that one of skill in the art could find other substances which activate the pathway, and the extent of such activation could be measured in vitro by determining increases of the various materials such as MAP-kinase, tyrosine phosphate, and the like along this pathway.

It will thus be appreciated that the present invention provides an immunotherapeutic agent comprising a low molecular weight glyco protein, which is of low toxicity and is highly effective as an anti-tumor agent, adjuvant and immune system stimulant. The agent of the present invention has significant utility as a research and therapeutic material.

It will be appreciated that the foregoing discussion and description is merely illustrative of particular embodiments to the present invention, and is not meant to be a limitation upon the practice thereof. It is the following claims, including all equivalents, which define the scope of the invention.

I claim:

1. A method of preparing an immunotherapeutic agent comprising the steps of:
    culturing cells of a bacterium selected from the group consisting of E. coli, and members of the genus Mycobacterium;
    collecting the cells of said bacterium;
    disrupting the membranes of said cells;
    separating said disrupted cells into sediment and supernatant liquid;
    flocculating the supernatant liquid;
    separating a solid material from the flocculated supernatant liquid; and
    separating said solid material into a first fraction having a molecular weight of about 85,000 daltons and a second fraction having a molecular weight of less than 85,000 daltons, wherein said immunotherapeutic agent comprises said second fraction.

2. A method as in claim 1, wherein the step of culturing cells of a bacterium comprises culturing cells of M. tuberculosis.

3. A method as in claim 1, wherein the step of disrupting the membranes of said cells comprises suspending said cells in water and ultrasonically disrupting their membranes.

4. A method as in claim 1, wherein the step of separating said disrupted cells comprises centrifuging said disrupted cells.

5. A method as in claim 1, wherein the step of flocculating the supernatant liquid comprises: freeze drying the supernatant to produce a dry material, dissolving the dry material in water at a concentration of approximately 20 milligrams per milliliter, and adding cold acetone to said water in a ratio of 2 parts acetone to 1 part water.

6. A method as in claim 1, wherein the step of separating a solid material from the flocculated supernatant liquid comprises centrifuging said flocculated supernatant liquid.

7. A method as in claim 1, wherein the step of separating said solid material comprises dissolving said solid material in water and passing said dissolved solid material through an ultrafilter.

8. An immunotherapeutic agent obtained from bacteria by a process comprising:
    culturing cells of a bacterium selected from the group consisting of members of the genus Mycobacterium, and E. coli;
    collecting the cells of said bacterium;
    disrupting the membranes of said cells;
    separating said disrupted cells into sediment and supernatant liquid;
    flocculating the supernatant liquid;
    separating a solid material from the flocculated supernatant liquid; and
    separating said solid material into a first fraction having a molecular weight of about 85,000 daltons and a second fraction having a molecular weight of less than 85,000 daltons, wherein said immunotherapeutic agent is present in said second fraction.

9. An immunotherapeutic agent as in claim 8, which incudes a low molecular weight glycopeptide which has a molecular weight of 919.2 daltons and a basic structure represented by the formula:

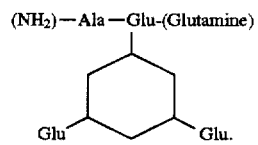

10. An immunotherapeutic agent as in claim 8, which includes a glycosylated protein having a molecular weight of approximately 65,000 daltons.

11. A method for stimulating the immune system of a cell comprising activating the intercellular RAS/RAF-1/MAP-kinase pathway of said cell.

12. A method as in claim 11, wherein the step of activating said RAS/RAF-1/MAP-kinase pathway comprises exposing said cell to an immunotherapeutic agent obtained from bacteria by a process comprising:
    culturing cells of a bacterium selected from the group consisting of members of the genus Mycobacterium, and E. coli;
    collecting the cells of said bacterium;
    disrupting the membranes of said cells;
    separating said disrupted cells into sediment and supernatant liquid;
    flocculating the supernatant liquid;
    separating a solid material from the flocculated supernatant liquid; and
    separating said solid material into a first fraction having a molecular weight of about 85,000 daltons and a second fraction having a molecular weight of less than 85,000 daltons, wherein said immunotherapeutic agent is present in said second fraction.

* * * * *